United States Patent [19]

Izumi et al.

[11] Patent Number: 4,677,845
[45] Date of Patent: Jul. 7, 1987

[54] DEVICE FOR DETECTING VISCOSITY OF LIQUID

[75] Inventors: Kouji Izumi, Yokohama; Masanori Horike, Tokyo; Tatsuya Furukawa, Yokohama; Hiromichi Komai, Yokohama; Osamu Naruse, Hatano; Yutaka Ebi, Kawasaki, all of Japan

[73] Assignee: Ricoh Company, Ltd., Tokyo, Japan

[21] Appl. No.: 804,612

[22] Filed: Dec. 5, 1985

[30] Foreign Application Priority Data

Dec. 7, 1984 [JP] Japan ................................ 59-259612

[51] Int. Cl.⁴ .............................................. G01N 11/04
[52] U.S. Cl. .............................................. 73/56; 137/92
[58] Field of Search ........................ 73/56, 55; 137/92

[56] References Cited

U.S. PATENT DOCUMENTS

| | | | |
|---|---|---|---|
| 1,178,193 | 4/1916 | Trimbey | 73/55 X |
| 1,544,705 | 7/1925 | Wallace | 73/56 X |
| 1,925,833 | 9/1933 | French | 73/56 X |
| 2,902,858 | 9/1959 | Leib | 73/55 |
| 3,187,563 | 6/1965 | Tobias | 73/56 |
| 3,344,799 | 10/1967 | Hardin | 73/56 X |
| 3,680,362 | 8/1972 | Geerdes et al. | 73/56 |

FOREIGN PATENT DOCUMENTS

| | | | |
|---|---|---|---|
| 2010252 | 10/1970 | Fed. Rep. of Germany | 73/56 |
| 393793 | 11/1965 | Switzerland | 73/56 |
| 1379470 | 1/1975 | United Kingdom | 73/56 |

Primary Examiner—Stewart J. Levy
Assistant Examiner—Joseph W. Roskos
Attorney, Agent, or Firm—Oblon, Fisher, Spivak, McClelland & Maier

[57] ABSTRACT

A device for detecting viscosity of a liquid which varies with time includes a first tank provided with an overflow section for maintaining a predetermined liquid height, and a second tank fluidly communicated to the first tank and provided with a restricted outlet, or orifice. While a liquid is circulated through the two tanks by a pump, a height sensor which is dipped in the liquid in the second tank senses a liquid height in the tank in terms of capacitance. The output of the height sensor is representative of a viscosity of the liquid.

5 Claims, 2 Drawing Figures

DEVICE FOR DETECTING VISCOSITY OF LIQUID

BACKGROUND OF THE INVENTION

The present invention relates to an ink jet printer or like equipment having a liquid supply system installed therein and, more particularly, to a device for continuously detecting the kinematic viscosity of a liquid flowing through the liquid supply system which varies with time.

In an ink jet printer, for example, ink is pumped from an ink supply system to an ink jet head and, by the action of an electrostrictive vibrator, ejected from a nozzle of the head. At a predetermined position ahead of the nozzle, a drop is separated from the jet of ink and charged to a predetermined polarity by a charging electrode. The charged drop is deflected by deflection electrodes to impinge on a recording medium to print out a dot thereon. The prerequisite with the ink jet printer is that drops be separated in a stable manner from the jet to be accurately charged, thereby enhancing quality printout of images. As well known in the art, the separation of drops from an ink jet greatly depends upon the viscosity of ink. Specifically, an ink jet printer of the type described is constructed to recirculate ink by collecting non-printing drops which do not contribute to printout using a gutter. The problem with such a recirculation scheme is that a solvent contained in the ink is evaporated during the flight of drops through the air, with the ink's viscosity gradually increasing in the course of repeated collection. The ink's viscosity is also susceptible to the ambient temperature. Such variations in the ink's viscosity is reflected by unstable separation of drops from a jet which in turn results in inaccurate charging.

An approach heretofore proposed to maintain ink viscosity constant relies on a flowmeter, as disclosed in Japanese Unexamined Patent Publication (Kokai) No. 58-20453/1983. Specifically, a conduit provides fluid communication between an ink reservoir and a pump so that the flow rate of ink circulated through the pipe, which is effected by the resistance of ink due to the ink's viscosity, is measured by the flowmeter. Based on the result of measurement, a solvent is supplied to the ink to control the viscosity to a predetermined one. Such a flowmeter scheme, however, attains only a limited degree of accuracy. In addition, the result of measurement is influenced by fluctuations of pump pressure.

Another approach known in the art uses a float which is dipped in ink so as to measure the specific gravity of the ink, as described in Japanese Unexamined Patent Publication (Kokai) No. 57-12685/1982. This float scheme also fails to accomplish accurate viscosity detection because it detects ink viscosity in terms of specific gravity.

SUMMARY OF THE INVENTION

It is therefore an object of the present invention to provide a liquid viscosity detecting device which accurately and continuously detects the viscosities of a liquid which flows through a liquid supply system, so that the liquid viscosity may be controlled to a predetermined one.

It is another object of the present invention to provide a generally improved device for detecting viscosity of a liquid.

A device for detecting viscosity of a liquid which is circulated through a liquid supply system of the present invention comprises a first tank supplied with the liquid and provided with a height regulator for maintaining a predetermined height of the liquid therein, a second tank communicated to the first tank by a conduit to be supplied with the liquid from the first tank, the second tank being provided with an orifice through which the liquid flows out, and a sensor for sensing a liquid height in the second tank, whereby viscosity of the liquid is detected in terms of an output of the sensor.

In accordance with this invention, a device for detecting viscosity of a liquid which varies with time includes a first tank provided with an overflow section for maintaining a predetermined height of the liquid. A second tank is fluidly communicated to the first tank and is provided with a restricted outlet, or orifice. While a liquid is circulated through the two tanks by a pump, a height sensor which is dipped in the liquid in the second tank senses a liquid height in the tank by way of a capacitance sensor. The output of this height sensor is representative of a viscosity of the liquid.

The above and other objects, features and advantages of the present invention will become more apparent from the following detailed description taken with the accompanying drawings.

DESCRIPTION OF THE PREFERRED EMBODIMENT

While the device for detecting liquid viscosity of the present invention is susceptible of numerous physical embodiments, depending upon the environment and requirements of use, a substantial number of these alternative embodiments as shown and described herein have been made, tested and used, and all have performed in an eminently satisfactory manner.

Figure 1:
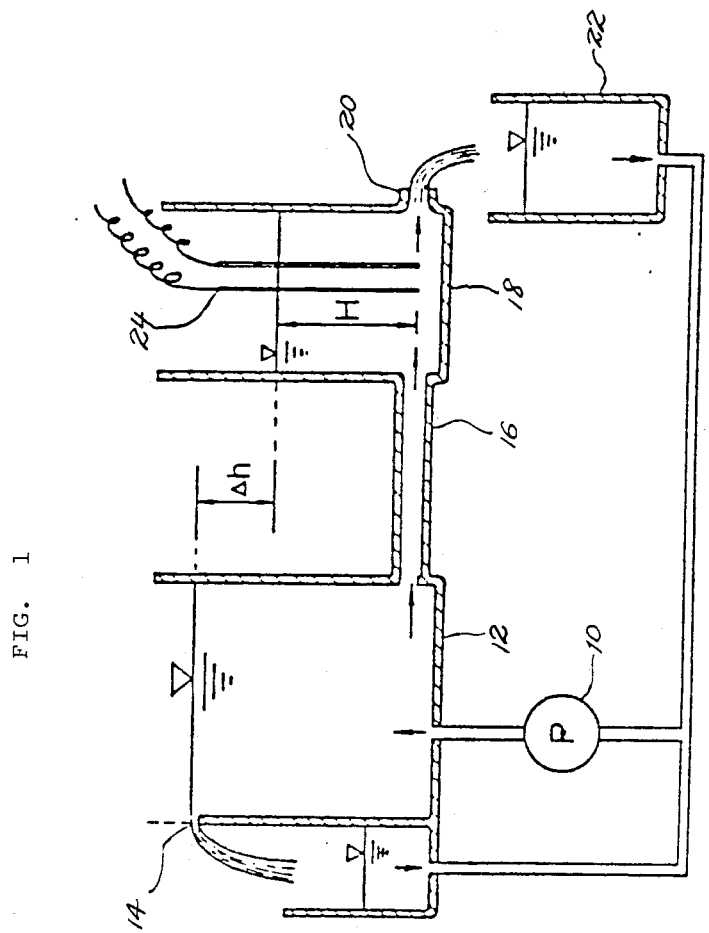
FIG. 1 is a schematic diagram of a liquid viscosity detecting device embodying the present invention which is applied to an ink jet printer.

Referring to FIG. 1 of the drawings, a viscosity detector in accordance with one embodiment of the present invention is shown which is applied to an ink jet printer by way of example. An ink circulation system includes a constant flow rate type pump 10 for pumping ink. The ink from the pump 10 is fed to a head tank 12 which is provided with an overflow section 14 in an upper portion thereof. The overflow section 14 may be implemented by a triangular weir, for example. The ink in the head tank overflows through the overflow section 14 in order to maintain a constant head. The ink in a lower portion of the head tank 12 is routed by a conduit 16 to a tank 18 which is provided with an orifice 20. The ink coming out through the orifice 20 is returned to the pump 10 by way of a tank 22. As shown, that part of the ink which overflows the head tank 12 is also returned to the pump 10. Disposed in the tank 18 is an implement 24, for measuring the height H of the ink in the tank 18. Specifically, the implement 18 comprises conductors each being coated with plastic and dipped in the ink so as to detect capacitance. This makes use of the fact that the ink level in the tank 18 has a linear relationship with the capacitance of the conductors.

Leads (not shown for clarity) extend out from the respective conductors of the implement 24.

Now, assuming that the ink flows into the tank 18 at a rate of Qin per unit time and flows out of the same at a rate of Qout, that the tank 18 has a cross-sectional area of S, and that the height in the tank 18 is H, then the following relationship holds:

$$S \frac{dH}{dt} = Q\text{in} - Q\text{out} \qquad \text{Eq. (1)}$$

The flow rate Qin of the ink from the conduit 16 into the tank 18 may be calculated as follows using the Hagen-Poiseuille's law:

$$Q\text{in} = \frac{\pi \Delta p}{8 \nu l} \cdot \left(\frac{di}{2}\right)^4 = \frac{\pi \rho g \Delta h}{8 \nu l} \cdot \left(\frac{di}{2}\right)^4 \qquad \text{Eq. (2)}$$

where $\nu$ is the kinematic viscosity coefficient of the ink, l the length of the conduit 16, di the inside diameter of the conduit 16, $\rho$ the density of the ink, $\Delta p$ the pressure difference between the tanks 12 and 18, $\Delta h$ the difference in liquid height between the tanks 12 and 18, and g the gravitational acceleration.

Meanwhile, the flow rate Qout is expressed, using Torricelli's theorem, as follows:

$$Q\text{out} = So \cdot Co \sqrt{2gH} \qquad \text{Eq. (3)}$$

where So is the cross-sectional area of the orifice 20, and Co the flow rate coefficient of the orifice 20.

From Eqs. (1), (2) and (3) above, it follows that if the incoming flow rate Qin is larger than or smaller than the outgoing flow rate Qout, the height H increases or decreases and, if the flow rates Qin and Qout are equal, the height H is held in equilibrium in which case the kinematic viscosity of the ink is the predominant factor which determines the height H. Hence, the ink viscosity can be accurately detected by determining the height H of a tank 18. In the production environment, however, it is the requisite that the fluctuation of the overflow height in the tank 12 be negligibly small. The pump 10, therefore, needs to be of the type which fulfills a condition Qover<<Qin, where Qover is the overflowing flow rate.

Figure 2:
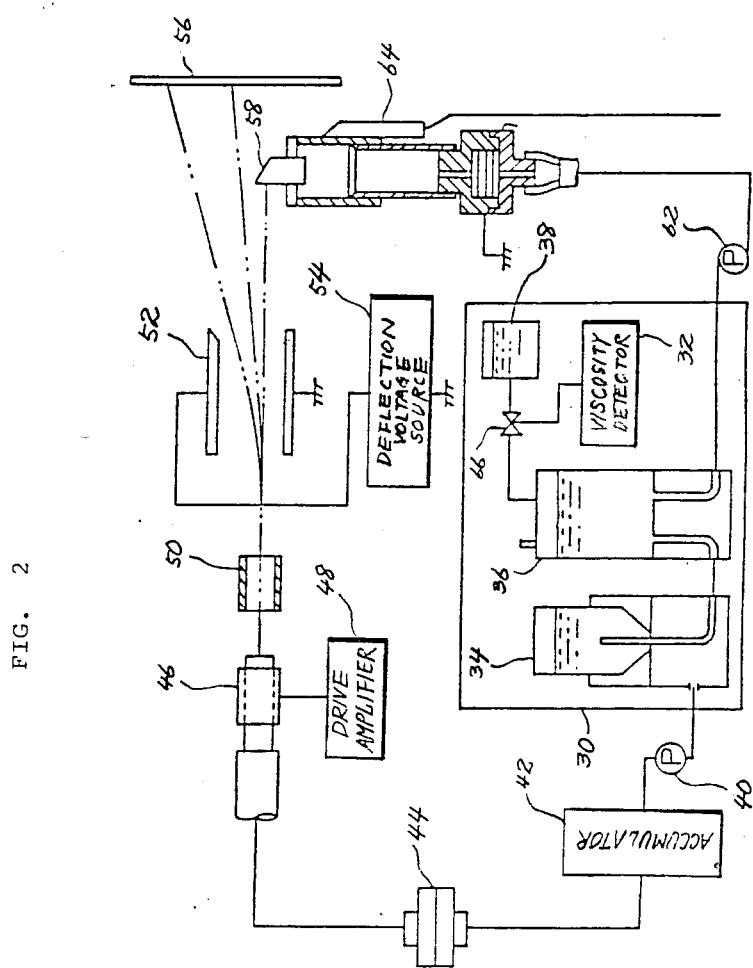
FIG. 2 is a schematic diagram of an ink jet printer in which the device of FIG. 1 is installed.

Referring to FIG. 2, an ink jet printer is shown which incorporates the viscosity detector of FIG. 1. The viscosity detector is included in a reservoir section 30 of the ink jet printer and generally designated by the reference numeral 32. Also included in the reservoir section 30 are an ink cassette 34, an ink tank 36 and a diluent tank 38. A pump 40 compresses ink which is supplied thereto from the reservoir section 30. The ink under pressure is routed through an accumulator 42 and a filter 44 to an ink jet head 46. The head 46 is driven by a drive amplifier circuit 48 to eject the ink. Printing drops which contribute to printout are charged by a charging electrode 50 and then deflected by deflection electrodes 52, which are biased by a deflection voltage source circuit 54, and thereby caused to impinge on a paper 56. Meanwhile, non-printing drops which do not contribute to printout advance straight toward a gutter 58 without being charged or deflected. The non-printed drops collected by the gutter 58 are routed through a filter 60 toward a pump 62 and then back to the ink tank 36. The reference numeral 64 designates a charge detecting electrode adapted to decide whether the separation of drops from the jet is adequate.

The tank 38 storing diluent therein is fluidly communicated to the ink tank 36 through a valve 66, which is controlled by the viscosity detector 32 of the present invention. The viscosity detector 32 continuously senses the ink viscosity in the ink tank 36 and, as the viscosity increases beyond a predetermined value, opens the valve 66 so that the diluent is supplied from the tank 38 to the tank 36 to control the ink viscosity to the predetermined one.

In summary, it will be seen that the present invention provides a liquid viscosity detecting device which accurately detects liquid viscosity to promote adequate control over the liquid viscosity and, thereby, quality printout. It is to be noted that, while the device of the present invention has been shown and described in relation to an ink jet printer, it is applicable to any other equipment having a fluid circulation system for continuously detecting kinematic viscosity which varies with time.

Various modifications will become possible for those skilled in the art after receiving the teachings of the present disclosure without departing from the scope thereof.

What is claimed is:

1. A device for detecting the viscosity of a liquid which circulated through a liquid supply system comprising:
   a first tank for holding said liquid;
   a supply means for supplying said liquid to said first tank;
   a height regulator means coupled to said supply means for maintaining at a predetermined height said held liquid;
   a second tank;
   a conduit coupling said first and second tanks below the level of said held liquid for transferring said liquid from said first tank to said second tank;
   an orifice in said second tank for providing an outflow of said liquid;
   sensor means placed in said second tank and in direct contact with said liquid contained therein for sensing the height of said liquid in said second tank;
   viscosity detecting means coupled to said sensor for calculating the viscosity of said liquid in response to the output of said sensor.

2. A device as claimed in claim 1, wherein said height regulator means comprises a triangular weir provided in an upper portion of the first tank.

3. A device as claimed in claim 1, said sensor means comprises a pair of conductors each being coated with plastic and dipped in the liquid inside the second tank.

4. A device as claimed in claim 1, wherein the liquid comprises ink which is circulated through an ink supply system of an ink jet printer.

5. A device as in claim 4 further comprising:
   a third tank holding diluent;
   a valve coupled to said viscosity detecting means for supplying said diluent held in said third tank to said ink supply.

* * * * *